US012576043B2

(12) United States Patent
T.K. et al.

(10) Patent No.: US 12,576,043 B2
(45) Date of Patent: Mar. 17, 2026

(54) XANTHOPHYLL COMPOSITION COMPRISING LUTEIN AND ZEAXANTHIN WITH ENHANCED BIOAVAILABILITY

(71) Applicant: OMNIACTIVE HEALTH TECHNOLOGIES LIMITED, Mumbai (IN)

(72) Inventors: Sunil Kumar T.K., Pune (IN); Pravin Nalawade, Pune (IN); Jangir Mohan Lal, Pune (IN); Abhijeet Morde, Pune (IN); Ravindra Thakare, Pune (IN)

(73) Assignee: OMNIACTIVE HEALTH TECHNOLOGIES LIMITED, Mumbai (IN)

( * ) Notice: Subject to any disclaimer, the term of this patent is extended or adjusted under 35 U.S.C. 154(b) by 546 days.

(21) Appl. No.: 17/634,994

(22) PCT Filed: Oct. 10, 2020

(86) PCT No.: PCT/IB2020/059534
§ 371 (c)(1),
(2) Date: Feb. 14, 2022

(87) PCT Pub. No.: WO2021/074763
PCT Pub. Date: Apr. 22, 2021

(65) Prior Publication Data
US 2023/0255898 A1 Aug. 17, 2023

(30) Foreign Application Priority Data
Oct. 15, 2019 (IN) .............................. 201921041676

(51) Int. Cl.
*A61K 31/047* (2006.01)
*A61K 9/107* (2006.01)
*A61K 47/44* (2017.01)

(52) U.S. Cl.
CPC ............ *A61K 31/047* (2013.01); *A61K 9/107* (2013.01); *A61K 47/44* (2013.01)

(58) Field of Classification Search
CPC ....... A61K 31/047; A61K 9/107; A61K 47/44
See application file for complete search history.

(56) References Cited

U.S. PATENT DOCUMENTS

| | | | |
|---|---|---|---|
| 6,075,058 A | 6/2000 | Handelman | |
| 7,045,643 B2 | 5/2006 | Estrella De Castro et al. | |
| 8,425,948 B2 * | 4/2013 | Sethuraman .............. | A61P 9/10 424/725 |
| 9,271,520 B2 | 3/2016 | Deshpande | |
| 10,016,364 B2 | 7/2018 | Nocolosi et al. | |
| 10,485,833 B2 | 11/2019 | Kumar T. K. et al. | |
| 11,337,925 B2 | 5/2022 | Musaeus et al. | |
| 2003/0232892 A1 | 12/2003 | Guerra-Santos et al. | |
| 2007/0265351 A1 | 11/2007 | Kumar T.K. et al. | |
| 2012/0108673 A1 | 5/2012 | Sethuraman et al. | |
| 2016/0143332 A1 | 5/2016 | Deshpande et al. | |
| 2018/0280266 A1 | 10/2018 | Deshpande et al. | |
| 2023/0255898 A1 | 8/2023 | Thattaruparambil Krishna Das et al. | |

FOREIGN PATENT DOCUMENTS

| | | | |
|---|---|---|---|
| AU | 2020368221 B2 | 4/2022 | |
| CN | 101781240 A | 7/2010 | |
| CN | 102481011 A | 5/2012 | |
| CN | 114502147 A | 5/2022 | |
| EP | 2601848 A1 * | 6/2013 | ........... A23D 7/0053 |
| EP | 4045019 A1 | 8/2022 | |
| JP | 2002-129057 A | 5/2002 | |
| JP | 2005-512587 A | 5/2005 | |
| JP | 2005-516049 A | 6/2005 | |
| JP | 2006-522739 A | 10/2006 | |
| JP | 2009-500309 A | 1/2009 | |
| JP | 2009-501802 A | 1/2009 | |
| JP | 2011-241176 A | 12/2011 | |
| JP | 2013-503844 A | 2/2013 | |
| JP | 2016-029031 A | 3/2016 | |
| JP | 2016-523933 A | 8/2016 | |
| JP | 2017-511380 A | 4/2017 | |
| WO | 99/047001 A1 | 9/1999 | |
| WO | WO 2011027209 A1 | 3/2011 | |
| WO | WO 2017056024 A1 | 4/2017 | |

(Continued)

OTHER PUBLICATIONS

Search Strategy dated Apr. 22, 2021 in the file history of the corresponding international application.
International Search Report dated Apr. 22, 2021.
Written Opinion of the International Searching Authority dated Apr. 22, 2021.
First Chinese Office Action and Search Report, issued in the corresponding Chinese patent application No. 202310267033.1, dated Apr. 15, 2024, 18 pages with the machine translation.
Second Chinese Office Action, issued in the corresponding Chinese patent application No. 202310267033.1, dated Aug. 26, 2024, 14 pages with the machine translation.

(Continued)

*Primary Examiner* — Zohreh A Fay
(74) *Attorney, Agent, or Firm* — HSML P.C.

(57) ABSTRACT

The present invention relates to a xanthophyll composition comprising selective isomers of trans-R,R lutein and trans-R,R zeaxanthin in preferred particle size and pharmaceutically and/or nutraceutically acceptable excipients such as carriers, solubility enhancers, bioavailability enhancing agents, antioxidants and optionally flavoring agents with selective ratio which exerts enhanced bioavailability. The xanthophyll composition at least 80% of total xanthophyll comprised of at least 65% by weight of trans-R,R lutein and at least 10% by weight of trans-R,R zeaxanthin, which is prepared combinedly from marigold and paprika oleoresins with definite proportion to produce the preferred ratio of trans-R,R lutein and trans-R,R zeaxanthin.

12 Claims, 6 Drawing Sheets

(56)                    References Cited

FOREIGN PATENT DOCUMENTS

WO          2021/074763 A1      4/2021

OTHER PUBLICATIONS

Chinese Rejection Decision, issued in the corresponding Chinese patent application No. 202310267033.1, dated Jan. 9, 2025, 15 pages with the machine translation.

First Chinese Office Action and Search Report, issued in the corresponding Chinese patent application No. 202080071064.4, dated Apr. 19, 2023, 17 pages with the machine translation.

First Japanese Office Action and Search Report, issued in the corresponding Japanese patent application No. 2022-520052, dated Dec. 19, 2023, 30 pages with the machine translation.

Second Japanese Office Action, issued in the corresponding Japanese patent application No. 2022-520052, dated Jun. 18, 2024, 6 pages with the machine translation.

Extended European Search Report, issued in the corresponding European patent application No. 20876997, dated Nov. 2, 2023, 4 pages.

Canadian Office Action, issued in the corresponding Canadian patent application No. 3151524, dated Nov. 21, 2024, 5 pages.

Australian Office Action, issued in the corresponding Australian patent application No. 2020368221, dated Feb. 19, 2024, 4 pages.

* cited by examiner

XANTHOPHYLL COMPOSITION COMPRISING LUTEIN AND ZEAXANTHIN WITH ENHANCED BIOAVAILABILITY

CROSS REFERENCE TO RELATED APPLICATIONS

This application is a U.S. National Stage application of PCT International Patent Application Number PCT/IB2020/059534, which was filed on Oct. 10, 2020, which claims the benefit of priority of the Indian patent application 201921041676, filed on Oct. 15, 2019, 2019, the disclosure of all of which is incorporated herein by reference.

FIELD OF THE INVENTION

The present invention mainly relates to a Xanthophyll composition comprising of selective isomers of lutein and zeaxanthin with a pharmaceutically and/or nutraceutically acceptable excipients and solubility enhancers, antioxidants with bio-enhancing agents enhancing the bioavailability of actives. This invention specifically relates to Xanthophyll composition comprising of selective trans-R,R lutein and trans-R,R zeaxanthin and at least one bioavailability enhancing agent, solubility enhancer, and an antioxidant. The invention further relates to a xanthophyll composition comprised of more than 80% of total xanthophylls, which is comprised of selective isomers such as trans-R,R lutein and trans-R,R zeaxanthin. The invention more specifically relates to the xanthophyll composition comprised of at least 80% by weight of trans-R,R lutein and at least 15% by weight of trans-R,R zeaxanthin, which is prepared by process of extraction from two different plant sources using industrially viable process. The invention further relates to the enhancement in bioavailability of xanthophyll composition comprising trans-R,R lutein and trans-R,R zeaxanthin by combination of micronization process to obtain selective range of particle size in preferred oil as a vehicle/carrier and selective solubility enhancer, antioxidant and bio-enhancing agent. This surprisingly improved bioavailability is due to combined effect of micronization process to obtain selective range of particle size in preferred oil as a vehicle and selective bio-enhancing agent with solubility enhancement and antioxidant which surprisingly exerts improvement in bioavailability. This invention further relates to xanthophyll composition comprising trans-R,R isomers of lutein and zeaxanthin in specific ratio that can be further formulated in different forms like beadlets, powders, oil suspensions, granules, capsules, tablets, films or any other suitable oral, parenteral or topical dosage forms using pharmaceutically or nutraceutically acceptable excipients or carriers or mixtures thereof. The invention further relates to xanthophyll composition, which is substantially free from R,S zeaxanthin and is suitable for human consumption to be used in various eye and brain health applications.

BACKGROUND OF THE INVENTION

The natural xanthophylls are amply present in and derived from various plant and animal sources. The beneficial health effects of natural xanthophylls and their antioxidant nature are well documented throughout scientific literature. The only hindrance to the effective utilization of these properties by the body is the low bioavailability and highly oxidizable nature of these nutrients. Understanding the long felt need of bioavailability, helps optimize doses for wellness supplements and drugs.

The oral bioavailability of many xanthophyll nutrients is limited due to physicochemical and physiological processes such as low solubility in gastrointestinal fluids; molecular structures, metabolizing enzymes causing chemical transformation within the gastrointestinal tract; low epithelium cell permeability, membrane transporters, interaction with the gut microbiota, and the like. The bioavailability of these agents can be improved by specifically designing the compositions that control their release, solubilization, transport, metabolism, and absorption within the gastrointestinal tract. Various approaches have been used to combat these problems of low bioavailability of the macular nutrients for their use in the form of nutraceutical products for human or veterinary use but there is strong felt need to improve the bioavailability. The approaches include composition comprising of trans-R,R zeaxanthin along with trans-R,R lutein in specific weight percentage which is prepared from extracts of two different plant sources using food grade solvents and industrially viable process of extraction, treatment with alkali, neutralization, purification and further formulating with selective particle size by micronization and preferred carrier or vehicle with bioavailability enhancing agent which provides a combination effect resulting in enhanced bioavailability.

U.S. Pat. No. 6,075,058A teaches compositions for increased bioavailability of carotenoids. The US patent teaches a mixture of 200 micrograms of the carotenoid lutein and 125 micrograms of the carotenoid zeaxanthin, along with the 10 mg of cholesterol, 100 mg olive oil, 20 mg egg yolk phospholipid, 250 micrograms alpha-tocopherol, and 0.375 ml of 0.15 M aqueous sodium chloride solution.

WO1999/047001 relates to a method of increasing the absorption of carotenoids and, more specifically, to increasing the absorption and bioavailability of lutein and zeaxanthin in humans and poultry by the use of lysolecithin and lecithin.

IN 201821036199 relates to a purified xanthophyll composition comprising (trans R R)-lutein and (trans R,R)-zeaxanthin, which is comprised of more than 80% of total xanthophylls and a process for the preparation thereof. Purified xanthophyll composition is comprised of selective isomerssuch as at least 85% by weight of (trans R,R)-lutein and at least 15% by weight of (trans R,R)-zeaxanthin. The composition is prepared by process of extraction. It is industrially viable process and purified by employing food grade polar and nonpolar solvents. This invention mainly speaks on the process for preparation of composition and completely silent over the formulation composition.

The inventors of the present invention have carried out rigorous experiments to prepare a xanthophyll composition which is comprised of selective isomers of trans-R,R zeaxanthin along with trans-R,R lutein, which is prepared from extraction of two different plant sources and subjecting the xanthophyll ester rich extracts to treatment with alcoholic alkali. The resulting reaction mixture is then subjected to extraction, isolation and purification process with use of food grade polar and non-polar solvents to selectively get at least 15% by weight of trans-R,R zeaxanthin isomer in combination with at least 80% by weight of trans-R,R lutein in a xanthophyll composition.

The present inventors have found that the enhancement in bioavailability of xanthophyll composition comprising trans-R,R lutein and trans-R,R zeaxanthin is due to combined effect of micronization process to obtain selective range of particle size in preferred oil as a vehicle, selective bio-enhancing agent, solubility enhancer and antioxidant which surprisingly exerts improvement in bioavailability.

OBJECTS OF THE PRESENT INVENTION

The main objective of the present invention is to provide xanthophyll composition selectively comprising of trans-R,R zeaxanthin along with trans-R,R lutein in specific weight percentage which is prepared from extracts of two different plant sources using food grade solvents and industrially viable process and formulating with pharmaceutically and/or nutraceutically accepted excipients result in enhanced bioavailability.

The further main objective of the present invention is an enhancement in bioavailability of xanthophyll composition comprising trans-R,R lutein and trans-R,R zeaxanthin is due to combined effect of micronization process to obtain selective range of particle size in preferred oil as a vehicle with selective bio-enhancing agent, solubility enhancer and antioxidant which surprisingly exerts improved bioavailability.

The further objective of the present invention is to provide xanthophyll composition comprising trans-R,R isomers of lutein and trans-R,R isomers of zeaxanthin in specific ratio is further formulated in different forms like beadlets, powders, oil suspensions, granules, capsules, tablets, films or any other suitable oral, parenteral or topical dosage forms using pharmaceutically or nutraceutically acceptable excipients and/or carriers.

Another objective of the present invention is to provide xanthophyll composition of trans-R,R zeaxanthin along with trans-R,R lutein and selective bioenhancer showing enhanced bioavailability with 90% Confidence interval for test formulation being more statistically significant i.e. more than 80-125% criteria of bioequivalence to show superior bioavailability compared to reference formulation.

One more objective of the present invention is to provide xanthophyll composition comprised of at least 80% of total xanthophylls, which is further comprised of at least 80% by weight of trans-R,R lutein and at least 15% by weight of trans-R,R zeaxanthin.

One more objective of the present invention is to provide xanthophyll rich composition comprised of selective isomers such as trans-R,R zeaxanthin and trans-R,R lutein and which is substantially free from R,S and S,S zeaxanthin.

Still one more objective of the present invention is to provide a composition which is obtained from extracts of two different plant sources comprising xanthophyll esters which are prepared by treatment with food grade solvent in specific proportions by using specific reaction conditions with unit operations.

One more important objective of the present invention is to provide xanthophyll rich composition, which is prepared from extracts of two different plant sources such as Marigold and Paprika.

One more objective of the present invention is to provide a process for preparation of xanthophyll composition which is prepared by mixing two xanthophyll ester rich extracts in definite proportion and subjecting the reaction mixture to treatment with alcoholic alkali, followed by neutralization isolation, and purification process to get desired purity of xanthophyll composition.

One more objective of the present invention is to provide selection of particle size by micronization and further addition of suitable oil as a vehicle with selective bio-enhancer, solubility enhancer, antioxidant and optionally flavoring agent and mixing to obtain xanthophyll composition in the form of oil suspension.

One more objective of the present invention is to provide xanthophyll composition selectively comprising of trans-R,R zeaxanthin and trans-R,R lutein along with at least one pharmaceutically and/or nutraceutically accepted excipient to prepare beadlets.

One more objective of the present invention is to provide xanthophyll composition, which is substantially free from R,S and S,S zeaxanthin and is suitable for human consumption to be used in various eye and brain health applications.

SUMMARY OF THE PRESENT INVENTION

According to an aspect of the present invention, there is provided xanthophyll composition comprising:
- i) trans-R,R lutein in the range of 65-85% by weight;
- ii) trans-R,R zeaxanthin in the range of 10-30% by weight;
- iii) one or more carrier and/or vehicle in the range of 10-80% by weight;
- iv) one or more solubility enhancer in the range of 1-10% by weight
- v) one or more flavoring agentin the range of 1-5% by weight;
- vi) one or more bioavailability enhancing agent in the range of 1-10% by weight; and
- vii) one or more antioxidant agent in the range of 1-10% by weight.

wherein trans-R,R lutein and trans-R,R zeaxanthin extracted from marigold and paprika oleoresin and are present in the ratio of 4:1 to 6:1, preferably 5:1, and the said composition is substantially free from R,S and S,S zeaxanthin.

The present invention further extends to the process for preparation of formulation as oil suspension and beadlets.

BRIEF DESCRIPTION OF ACCOMPANYING FIGURES

According to FIGS. 1-8 the graphs designated as Product A (Micro OS R+) read as trans-R,R lutein and trans-R,R zeaxanthin composition. Reference is product B.

FIG. 1 demonstrates that Baseline corrected serum trans-R,R lutein concentrations for Micro OS R+ group were significantly higher ($P<0.05$) compared to Reference group between 2 to 72 hrs time points post dose.

Figure 3:
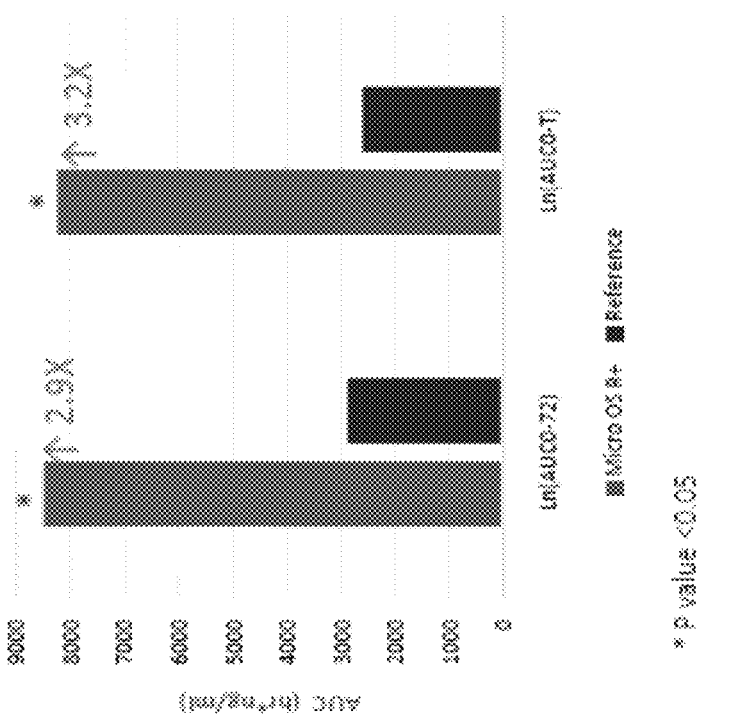
FIG. 3 shows trans-R,R lutein AUC0-72 & AUC0-T: Micro OS R+Vs Reference.
Figure 2:
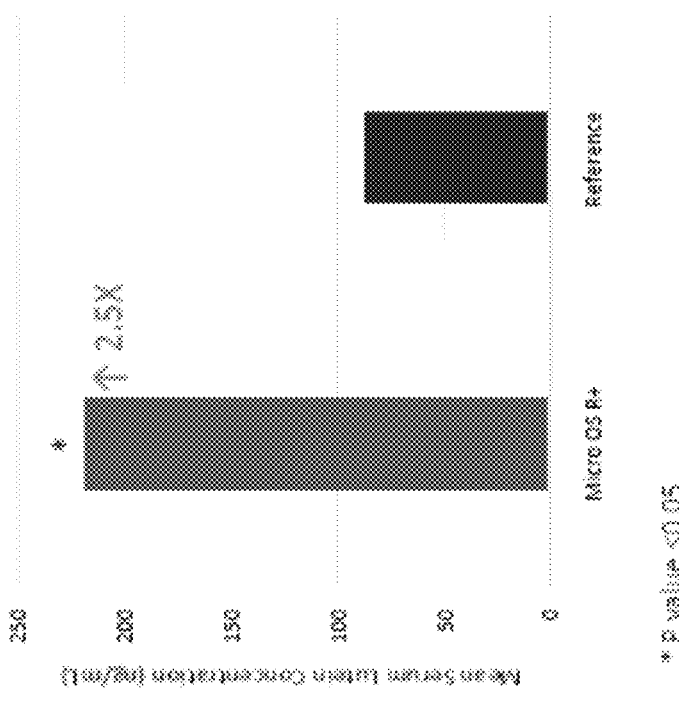
FIG. 2 shows trans-R,R lutein Pharmacokinetic Parameters—Cmax.

FIGS. 2 and 3 demonstrate that Micro OS R+ group showed significantly higher absorption for trans-R,R lutein compared to Reference group as evident from the 2.5× folds Cmax, 2.9× folds AUC0-72 and 3.2× folds AUC0-T levels.

Figure 4:
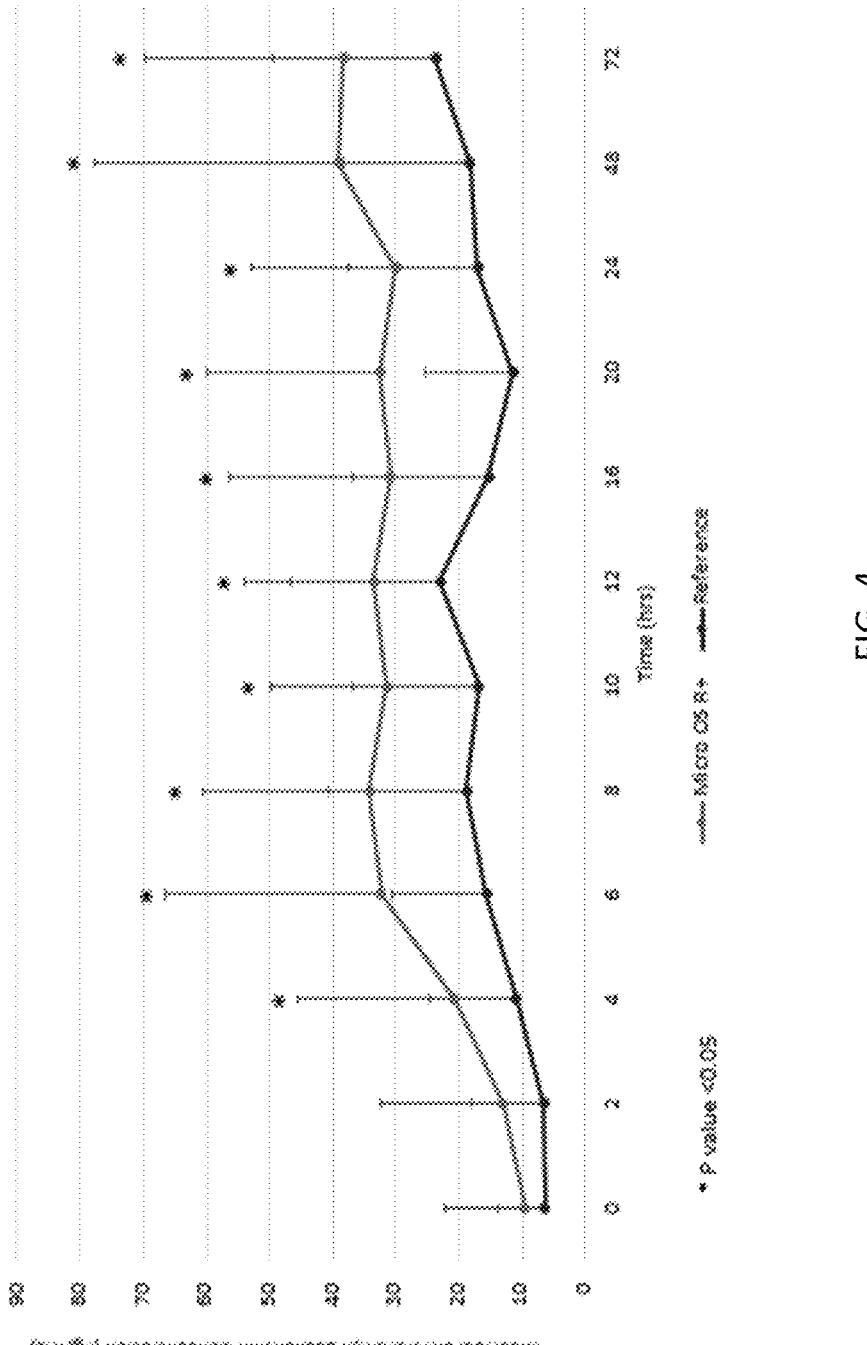

FIG. 4 shows Comparative linear Plot of Baseline Corrected Mean±SD of Serum trans-R,R zeaxanthin Concentrations vs Time for Micro OS R+ and Reference. FIG. 4 demonstrates that Baseline corrected serum trans-R,R Zeaxanthin concentrations for Micro OS R+ group were significantly higher ($P<0.05$) compared to Reference group between 4 to 72 hrs time points post dose.

Figure 5:
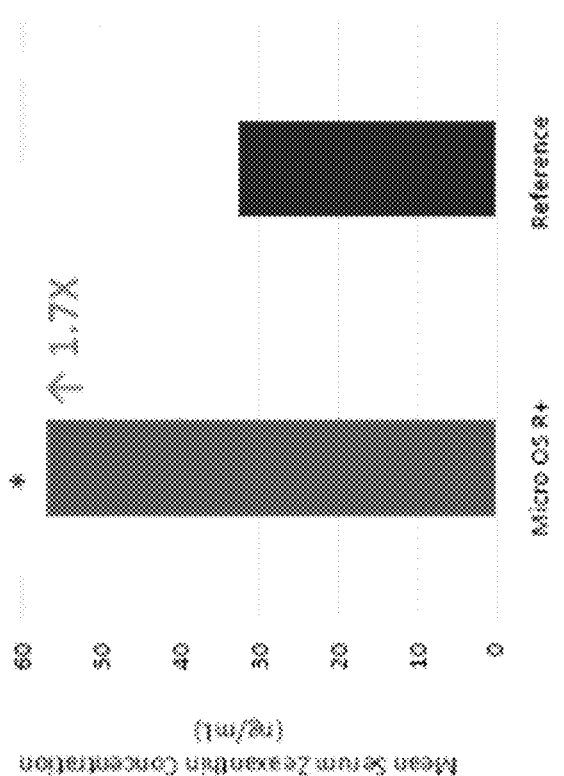

FIG. 5 shows trans-R,R zeaxanthin Pharmacokinetic Parameters—Cmax.

Figure 6:
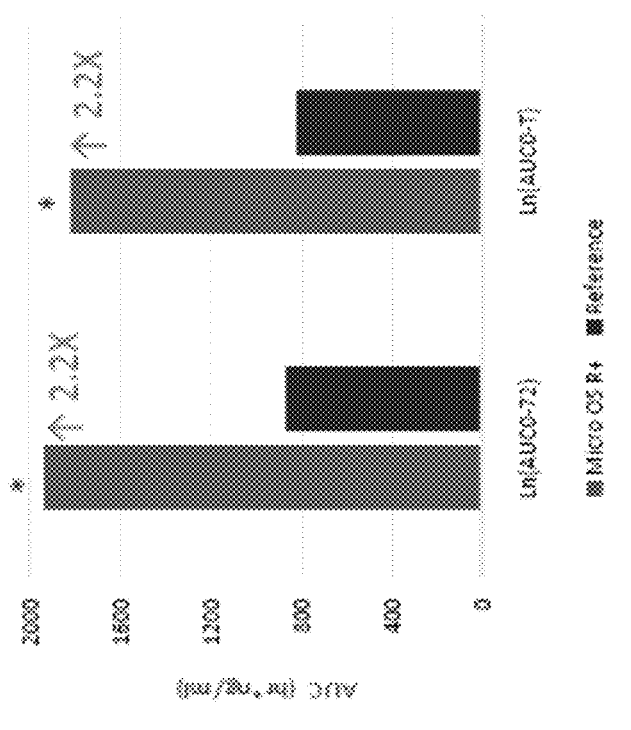

FIG. 6 shows trans-R,R zeaxanthin AUC0-72 & AUC0-T: Micro OS R+Vs Reference.

FIGS. 5 and 6 demonstrate that Micro OS R+ group showed significantly higher absorption for trans-R,R zeaxanthin compared to Reference group as evident from the 1.7× folds Cmax and 2.2× folds AUC0-72 & AUC0-T levels.

Figure 7:
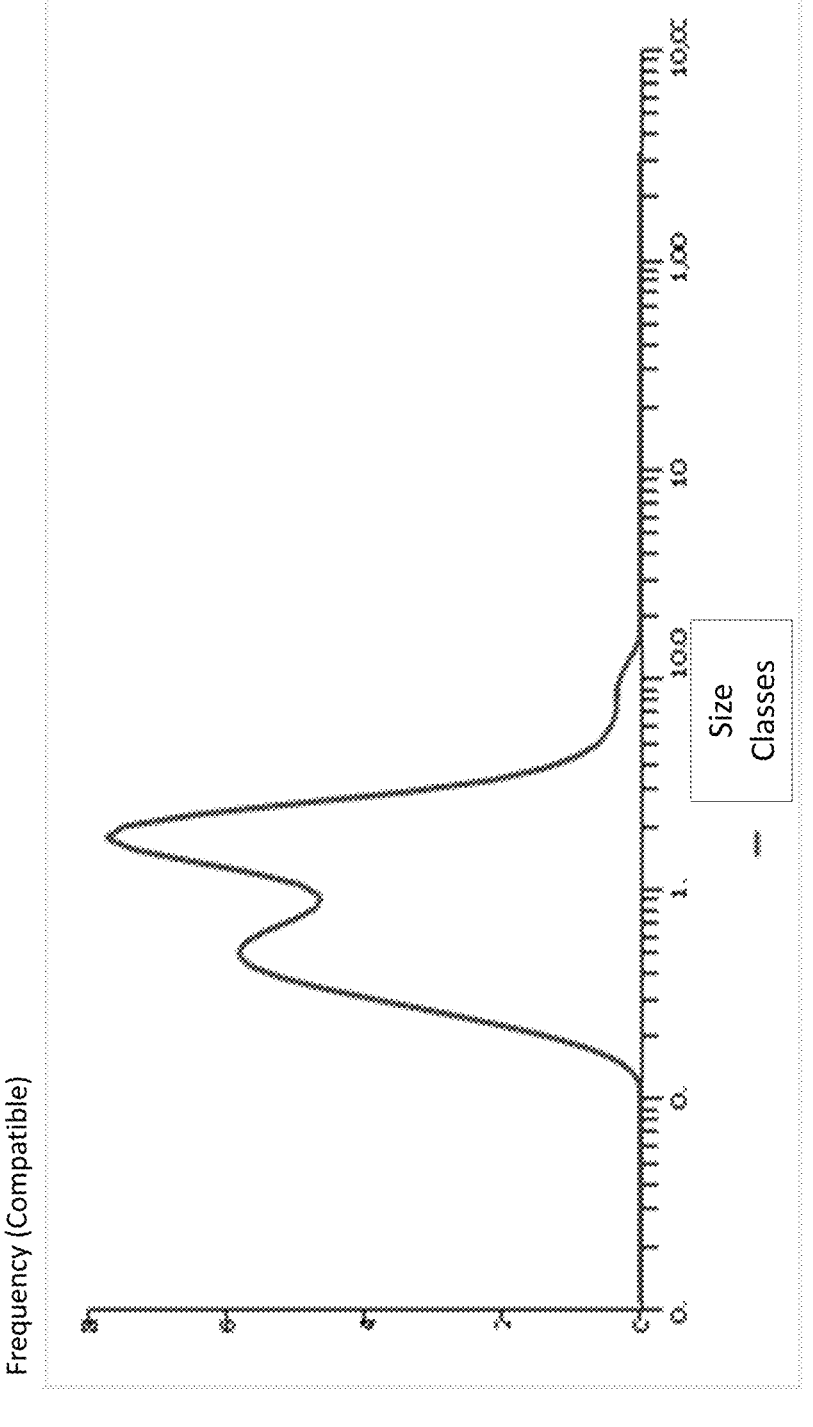

FIG. 7 shows particle size of trans-R,R lutein and trans-R,R zeaxanthin before preparation of oil suspension.

Figure 8:
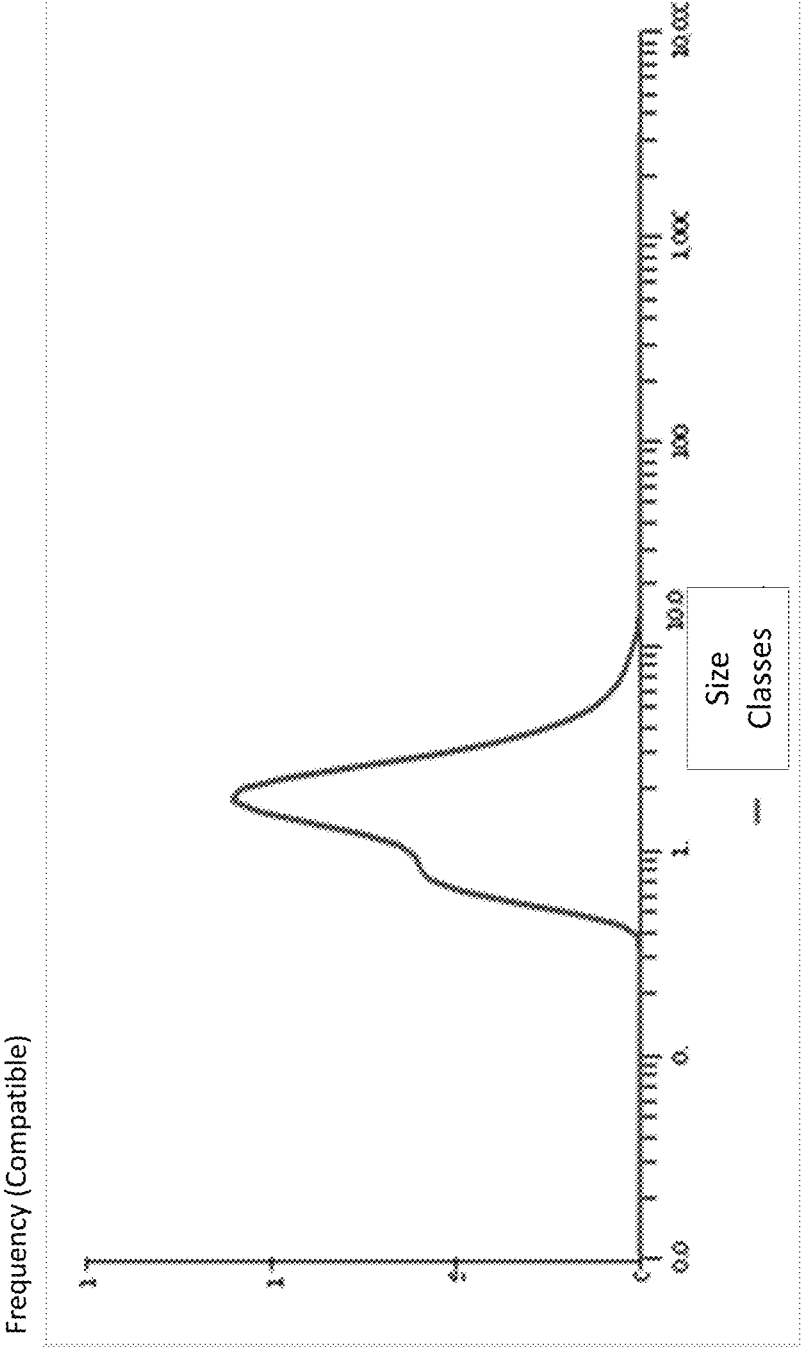

FIG. 8 shows particle size of trans-R,R lutein and trans-R,R zeaxanthin after preparation of oil suspension.

DETAILED DESCRIPTION OF PRESENT INVENTION

The present invention relates to a xanthophyll composition comprising selective isomers such as trans-R,R lutein and trans-R,R zeaxanthin and a process for the preparation thereof. The invention specifically relates to a xanthophyll composition comprised of more than 80% of total xanthophylls, which is further comprised of at least 80% by weight of trans-R,R lutein and at least 15% by weight of trans-R,R zeaxanthin. The process is comprised of mixing the extracts containing xanthophylls esters obtained from two different plant sources in definite proportion and further treated to get xanthophyll composition selectively comprised of trans-R,R lutein and trans-R,R zeaxanthin in desired percentage. The enhancement in bioavailability of xanthophyll composition comprising trans-R,R lutein and trans-R,R zeaxanthin is due to combined effect of micronization process to obtain selective range of particle size in preferred oil as a vehicle and selective bio-enhancing agent, solubility enhancer and anti-oxidant with flavoring agent which surprisingly exerts improvement in bioavailability in 1.5 to 4 fold against the reference. This xanthophyll composition comprising of trans-R,R isomers of lutein and trans-R,R isomers of zeaxanthin in specific ratio from 4:1 to 6:1 is further formulated in different forms like beadlets, powders, oil suspensions, granules, capsules, tablets, films or any other suitable oral, parenteral or topical dosage forms using pharmaceutically or nutraceutically acceptable excipients and/or carriers. The xanthophyll composition, which is substantially free from R,S and S,S zeaxanthin and is suitable for human consumption to be used in various eye and brain health applications.

According to embodiment of the present invention the xanthophyll composition selectively comprising of trans-R,R lutein and trans-R,R zeaxanthin in specific weight percentage which is prepared from extracts of two different plant sources using food grade solvents and industrially viable process treatment with alkali, neutralization, isolation, purification and then formulating with pharmaceutically and/or nutraceutically accepted excipients result in enhanced bioavailability.

Within the context of this invention, the term 'xanthophyll composition' means a composition comprised of xanthophylls such as selective isomers of lutein and zeaxanthin which is prepared from two different plant sources and purified by using food grade solvents, so that the composition is selectively comprised of trans-R,R lutein and trans-R,R zeaxanthin. More importantly the composition is substantially free from R,S and S,S isomer of zeaxanthin.

According to the main embodiment of the invention, the xanthophyll composition is selectively comprised of at least 80% by weight of total xanthophylls, of which at least 65-85% by weight being trans-R,R lutein and at least 10-30% by weight being trans-R,R zeaxanthin which is useful for nutrition and healthcare.

According to important embodiment of the invention, the plant material used for the extraction may be selected from various sources including, but not limited to, fruits, flowers and vegetables such as kiwi fruit, grapes, spinach, orange juice, zucchini (or vegetable marrow), and different kinds of squash, paprika, other dark green leafy vegetables, parsley, kale, egg yolk, maize and the like. As per one of the embodiments of the invention, the plant material selected for preparation of the composition is marigold flower (*Tagetes erecta*) and hybrid species of Paprika. Particularly lutein ester rich extract is obtained from marigold flower and zeaxanthin ester rich extract is obtained from specific variety of Paprika.

As per one more embodiment of the invention, marigold flowers containing specific percentage of xanthophyll content are selected and processed to get the pellets, which are extracted using food grade solvents under specific conditions. The extract containing about 14-17% by weight of lutein esters is obtained for further processing.

According to one more embodiment of the invention, fresh paprika fruit pods having R,R zeaxanthin content of around 0.04-0.08% by weight are selected and dried to specific moisture level and trans-R,R zeaxanthin content. Dried chili (paprika) are cut in small pieces to obtain powder, which is then treated with food grade solvent/s to get extract having 3-4% by weight of R,R zeaxanthin esters.

Marigold flowers (scientific name—*Tagetes erecta*, Family—Asteraceae): is a species of the genus *Tagetes* native to Mexico. It is cultivated in Asia, Africa and South America. Marigold is also cultivated in the districts of Karnataka, particularly in the area of Hassan, Chickamangaluru, Mysore, Chamrajnagar, Davangere. For further processing the Marigold flowers are delivered to plant situated at Hassan (Karnataka) and Kangayam (Tamilnadu) India. The extraction is carried out by manual intervention, in order to prepare a composition rich in xanthophyll, which selectively contains trans-R,R zeaxanthin isomer along with trans-R,R lutein in specific weight percentage, which is explicitly different from naturally existing composition of marigold flowers and thus is enriched and safe for human consumption.

Another source used in the invention is Paprika (*Capsicum annuum*) which is a species of the plant genus *Capsicum* (peppers) native to southern North America and northern South America. This species is the most common and extensively cultivated of the five domesticated capsicums. For the purpose of present invention, the raw material may be either purchased from outside of India, or may be cultivated as *Capsicum annuum* in Karnataka.

The xanthophyll composition is comprised of at least 80% by weight of total xanthophyll, of which at least 65% by weight being trans-R,R lutein and at least 10% by weight being trans-R,R zeaxanthin.

According to a preferred embodiment the composition is substantially free of R,S and S,S zeaxanthin.

In an embodiment, the xanthophyll composition is comprised of trans-R,R lutein and trans-R,R zeaxanthin in the ratio of 4:1 to 6:1.

In an embodiment, the xanthophyll composition is comprised of trans-R,R lutein and trans-R,R zeaxanthin in the ratio of 5:1.

In an embodiment, the xanthophyll composition is comprised of trans-R,R lutein 10 to 15 mg and trans-R,R zeaxanthin is 2 to 3 mg.

In an embodiment, the xanthophyll composition comprising trans-R,R lutein and trans-R,R zeaxanthin is in the range of 0.1-10 micron.

In an embodiment, the obtained oil suspension composition as per the example 1 having particle size is in the range of 0.1-10 micron.

In an embodiment, the xanthophyll composition comprising increased bioavailability of 1.5-4 folds against reference (Product B).

According to still one more embodiment of the invention, xanthophyll composition described herein can be formulated using at least one pharmaceutical, nutraceutical or food grade excipient or combination thereof. The excipient selected from bioavailability enhancing agent, carrier/vehicle, granulating agent, inert core, coating agent, solvent, diluents, binder, lubricant, disintegrant, antioxidant, oil, surfactant, solubilizer, emulsifier or any other excipient, which is known to a person skilled in the art as excipient required for preparing palatable dosage form, acceptable to the subject.

According to further embodiment of the present invention bioavailability enhancing agent may be selected from nigella (black cumin oil), caraway (*Carum carvi*) oil, Phosphatidyl choline (lecithin), starch sodium octenyl succinate, Allspice Berry, Amber Essence, Anise Seed, *Arnica*, Balsam of peru, Basil, Bay Leaf, Benzoin Gum, Bergamot, Bois de Rose (Rosewood), Cajeput, Calendula (Marigold pot), White Camphor, Caraway Seed, Cardamon, Carrot Seed, Cedarwood, Celery, German or Hungarian Chamomile, Roman or English Chamomile, Cinnamon, Citronella, Clary Sage, Clovebud, Coriander, Cumin, Cypress, *Eucalyptus*, Fennel, Siberian Fir needle, Frankincense (Olibanum oil), Garlic, Rose Geranium, Ginger, Grapefruit, Hyssop, Jasmine Absolute, Jojoba, Juniper Berry, Lavender, Lemon, Lemongrass, Lime, Sweet Marjoram, Mugwort, Mullein Flower, Myrrh Gum, Bigarade Neroli, Nutmeg, Bitter Orange, Sweet Orange, Oregano, Patchouly, Pennyroyal, Black Pepper, Peppermint, Petitegrain, Pine Needle, Poke Root, Rose Absolute, Rosehip Seed, Rosemary, Dalmation Sage, Sandalwood Oil, *Sassafras*, Spearmint, Spikenard, Spruce (Hemlock), Tangerine, Tea Tree, *Thuja* (Cedar leaf), Thyme, Vanilla extract, Vetivert, Wintergreen, Witch Hazel (Hamamelia) Extract, or Ylang (*Cananga*) Extract or the combination thereof.

According to a preferred embodiment of the present invention bioavailability enhancing agent selected from nigella (black cumin oil), caraway (*Carum carvi*) oil, Phosphatidyl choline (lecithin).

According to further embodiment the bioavailability enhancing agent present in range of 1-10% by weigh of composition.

According to further embodiment the bioavailability enhancing agent present in range of 1-5% by weigh of composition.

According to further embodiment the bioavailability enhancing agent present in range of 1-3% by weigh of composition.

According to a preferred embodiment of the present invention solubility enhancer may selected from thyme oil, olive oil, linseed oil (flaxseed oil) or mixture thereof.

According to further embodiment the solubility enhancer present in range of 1-10% by weigh of composition.

According to further embodiment the solubility enhancer present in range of 1-5% by weigh of composition.

According to further embodiment of the present invention antioxidant may be selected from but not limited to, but not limited to butylated hydroxytoluene, butylated hydroxyanisole, ascorbic acid, ascorbyl palmitate, sodium ascorbate, mixed tocopherol, alpha-tocopherol, beta-tocopherol, gamma-tocopherol, delta-tocopherol, synthetic racemic tocopherols and tocopherol esters or the combination thereof.

According to further embodiment the range of the antioxidant is 1-10% by weight of composition. According to further embodiment the antioxidant present in range of 1-10% by weight of composition. According to further embodiment the antioxidant present in range of 1-5% by weight of composition. According to further embodiment the antioxidant present in range of 1-3% by weight of composition.

According to further embodiment of the present invention carrier/vehicle may be selected from but not limited to sunflower oil, coconut oil, corn oil, cottonseed oil, canola oil, olive oil, palm oil, peanut oil, safflower oil, sesame oil, soybean oil, rapeseed oil and medium chain triglyceride (MCT) oil or the combination thereof.

According to further embodiment of the present invention Hydrophilic carrier may be selected from but not limited to celluloses such as alkyl cellulose (methyl cellulose), a hydroxyalkyl cellulose (e.g., hydroxymethyl cellulose, Hydroxypropyl cellulose), carboxyalkyl cellulose (e.g., carboxymethyl cellulose and alkali metal salts thereof, such as sodium salts), a carboxyalkylalkyl cellulose (e.g., carboxymethylethyl cellulose), carboxyalkyl cellulose ester (e.g., carboxymethyl cellulose butyrate, carboxymethyl cellulose propionate, carboxymethyl cellulose acetate butyrate and carboxymethyl cellulose acetate propionate) or the combination thereof.

Polyacrylates such as polymethacrylate, a methacrylate copolymer (e.g., a methacrylic acid-methyl methacrylate copolymer, dimethylaminoethyl methacrylate-butyl methacrylate-methyl methacrylate copolymer, and a diethylaminoethyl methacrylic acid-methyl methacrylate copolymer), and an ethacrylate copolymer (e.g. methacrylic acid ethacrylate copolymer) or the combination thereof; povidones such as polyvinyl pyrrolidone, polyvinyl acetate ester (e.g., polyvinyl acetate phthalate (PVAP), and polyethylene glycol polyvinylacetate copolymer (e.g. polyethylene glycol-polyvinylcaprolactam-polyvinylacetate copolymer) or the combination thereof.

Starch and starch derivatives such as Modified Starch, corn starch, potato starch, pregelatinized starch, dextrins, acid-treated starch, alkaline-treated starch, bleached starch, oxidized starch, enzyme-treated, monostarch phosphate, distarch phosphate, phosphateddistarch phosphate, acetylated distarch phosphate, starch acetate, acetylated distarch adipate, hydroxypropyl starch, hydroxypropyl distarch phosphate, hydroxypropyl distarch glycerol, starch sodium octenyl succinate, acetylated oxidized starch and maltodextrin or the combination thereof.

Gums such as pectin alginate, carrageenan agar, gum arabic, gum tragacanth, gum karaya, gum ghatti, gum guar, Locust bean gum, Tara gum, Xanthan gum, Gellan gum and Welan gum or the combination thereof; sugars such as fructans, sucrose, glucose and fructose or the combination thereof.

According to preferred embodiment the carrier is MCT oil. According to further embodiment MCT oilis present in range of 20-80% by weight of composition. According to further embodiment MCT oilis present in range of 50-70% by weight of composition.

According to preferred embodiment the carrier is modified starch. According to further embodiment starchis present in range of 10-40% by weight of composition.

According to further embodiment starchis present in range of 10-30% by weight of composition. According to further embodiment starchis present in range of 10-20% by weight of composition.

According to one embodiment, xanthophyll composition comprising trans enriched trans-R,R isomers of lutein and zeaxanthin in specific ratio can be further formulated in different forms like beadlets, powders, oil suspensions, granules, capsules, tablets, films or any other suitable oral, parenteral or topical dosage forms using pharmaceutically or nutraceutically acceptable excipients and/or carriers, but preferably oil suspension and beadlets.

As per one embodiment of present invention, the process for manufacture of beadlets is comprised of spraying carotenoid emulsion in a square chamber and embedding it in cold matrix bed, wherein square chamber has provision for continuous rotation and circulation of cold water through jacketed vessel.

As per one embodiment of the present invention, the process for preparation of carotenoid emulsion is comprised of solvent phase and aqueous phase and mixing the two phases under stirring at specific conditions to get emulsion. The solvent phase as described herein is prepared by dissolving active in solvent phase comprised of organic solvent, antioxidant and at least one more oily excipient, at specific conditions and filtering out to remove any insoluble residue. The aqueous phase as described herein is prepared by dissolving hydrophilic carrier and antioxidant in water.

As per one more embodiment of this invention, the solvent phase is added to water phase under stirring to get emulsion and homogenized in high pressure homogenizer. This homogenized emulsion is then subjected to evaporation under vacuum to get solvent free carotenoid emulsion.

As per one important embodiment of the present invention, the process for the manufacture of carotenoid beadlets is comprised of spraying carotenoid emulsion in square chamber, which is embedded and solidified in cold matrix bed to form the beadlets.

As per one more embodiment of this invention, the process for the manufacture of carotenoid beadlets is carried out in square chamber which has provision of two inlets at top for spray nozzle of emulsion and for hydrophilic matrix. The square chamber also has two outlets at bottom of chamber for collection of beadlets and unused matrix bed.

As per one more important embodiment of this invention, the square chamber has provision for continuous rotation as well as circulation of cold water through jacketed vessel to maintain inside temperature below 20° C.

As per the main embodiment of the present invention, the process for manufacture of carotenoid beadlets is comprised of loading the matrix bed through one inlet at the top of square chamber and maintaining it cold with the help of circulating cold water. The emulsion is sprayed through spray nozzle of rotating square chamber and the droplets are embedded in particles of cold matrix bed to form beadlets.

The beadlets formed by the above process are collected through outlet at the bottom of square chamber and subjected to drying until desired moisture level is attained.

As per one more embodiment of the present invention, matrix bed which is loaded in square spray chamber is selected from, but not limited to starch derivatives such as wax modified maize starch, starches and modified starches in combination with talc, silicic acid, hydrogenated fats, metal salt of higher fatty acid such as calcium stearate, aluminium silicate of alkali metal/alkaline earth metal, sodium or calcium aluminium silicate, alumina, calcium silicate, powdered silica gel, magnesium carbonate and magnesium oxide or the combination thereof.

As per a preferred embodiment of the present invention, the process for preparation of xanthophyll composition in the oil suspension form comprised of obtaining trans-R,R lutein and trans-R,R zeaxanthin with selective ratio of 4:1 to 6:1 by extracting from marigold and paprika oleoresin. The marigold and paprika extracted to get trans-R,R lutein and trans-R,R zeaxanthin called as concentrate which further undergoes for micronization by using air jet mill to obtain particle size in the range of 0.1-10 micron. The micronized trans-R,R lutein and trans-R,R zeaxanthin with selective ratio with preferred particle size obtained is mixed by adding bioavailability enhancing agent, solubility enhancer, antioxidant, carrier oil and optionally flavor using ball mill at room temperature. The obtained oil suspension composition has particle size in the range of 0.1-10 micron.

The particle size of the trans-R,R lutein and trans-R,R zeaxanthin is in the range of 0.1-10 micron.

The other excipient such as carrier oil/vehicle, bioavailability enhancing agent, solubility enhancer, stabilizer, and antioxidant is added in ball mill.

The particle size of obtained oil suspension composition as per the example 1 having particle size is in the range of 0.1-10 micron.

As per the further embodiment, the Xanthophyll composition in the form of oil suspension comprising Xanthophyll and pharmaceutically and/or nutraceutically acceptable excipient shaving enhanced bioavailability.

At the outset of the description that follows, it is to be understood that the ensuing description only illustrates a particular form of this invention. However, such a particular form is only an exemplary embodiment and is not intended to be taken restrictively to imply any limitation on the scope of the present invention.

Example 01

According to preferred embodiments we have performed different size batches from small to large scale to support the industrial viability in process.

Oil suspension composition preparation; Batch size 500 g

| | Batch size 500 g | | |
| --- | --- | --- | --- |
| Sr. No | Name of the Ingredient | Standard Quantity (g) | % W/W |
| 1 | Micronized trans-R,R lutein and trans-R,R zeaxanthin | 170 | 35 |
| 2 | Olive Oil USP | 25 | 5 |
| 3 | MCT Oil | 260 | 51 |
| 4 | Mixed Tocopherol 70%-SF | 10 | 2 |
| 5 | Thyme Oil | 5 | 1 |
| 6 | Linseed oil (flaxseed oil) | 10 | 2 |
| 7 | D-Limonene | 10 | 2 |
| 8 | Lecithin (Phosphatidylcholine) | 10 | 2 |

A weight quantity of marigold oleoresin (33.5 kg) containing 16.6% xanthophyll content (by spectrophotometric method) and 13.6 lutein content (by HPLC method). Paprika oleoresin (16.5 kg) containing 5.7% xanthophyll content (by spectrophotometric method) and 3.5% zeaxanthin content (by HPLC method).

Each oleoresin was added in reactor with aqueous alcoholic alkali solution (10 kg potassium hydroxide in 15 ltr water and 62.5 ltr of ethanol). The mixture was heated in reactor with stirring at 80° C. for a period of 4 hours. The degree of hydrolysis was monitored by HPLC during the reaction and reaction terminated by adding water 250 ltr. The homogenize the reaction mass at room temperature and add ethyl acetate (300 ltr) in reactor for liquid-liquid extraction and repeated the process for 3-5 times. The EA layer separated out and washed with water (1:1) at room temperature. The water washed ethyl acetate further taken for concentration and to get concentrated material. The concentrated material isolated by using hexane to the removing impurities and to get semi-purified crystals (22.5 kg) of xanthophyll composition. The semi-purified crystals obtained were purified with ethanol 5 volumes at room temperature, followed by filtration (7.8 kg). The resulting crystals were vacuum dried at temperature of about 50 to 55° C. for 36 hrs. The yield of the dried xanthophyll crystals was 9.6 kg (9.6%). The xanthophyll content was 87.2% by weight (UV/Vis-spectrophotometry) out of which the contents of trans-R,R lutein and trans-R,R zeaxanthin were 70.3%, and 14.4% and area % of trans-R,R lutein and trans-R,R zeaxanthin were 80.6%, and 16.5% respectively as determined by normal phase HPLC analysis.

The obtained concentrate (2.5 kg) containing 87.2% xanthophyll content (by spectrophotometric method) was taken for Micronization. The Micronization of marigold paprika extract concentrate containing particle size (DV90) 1690 μm was micronized by using air jet mill. The resulting micronized crystals (2.2 kg) containing particle size (DV50) 1.61 μm and (DV90) 3.24 μm (FIG. 8) and the xanthophyll content was 89.09% by weight (UV/Vis-spectrophotometry) out of which the contents of trans-R,R lutein and trans-R,R zeaxanthin were 71.62%, and 14.75% and area % of trans-R,R lutein and trans-R,R zeaxanthin were 80.39%, and 16.56% respectively as determined by normal phase HPLC analysis.

The micronized marigold paprika extract concentrate (170 g) containing 87.2% xanthophyll content (by spectrophotometric & HPLC method) was used to make formulation as oil suspensions. The micronized marigold paprika extract concentrate was mixed by adding oil (260 g) medium Chain triglycerides (MCT) with 14% (70 g) other ingredients as olive oil, thyme oil, linseed oil (flaxseed oil), D-Limonene, Lecithin (Phosphatidylcholine) (Obtained from Sunflower), mixed tocopherol by using ball mill at room temperature. The mixture was sieved and unloaded (500 g) analyzed for containing particle size (DV50) 1.04 μm and (DV90) 2.66 μm (FIG. 7) and xanthophyll content was 28.05% by weight (UV/Vis-spectrophotometry) out of which the contents of trans-R,R lutein and trans-R,R zeaxanthin were 22.64%, and 4.63% and area % of trans-R,R lutein and trans-R,R zeaxanthin were 80.72%, and 16.49% respectively as determined by normal phase HPLC analysis.

Example 02

Oil suspension preparation; Batch size 18 Kg

| | | Batch size 18.0 kg | | |
|---|---|---|---|---|
| Sr. No | Name of the Ingredient | | Standard Quantity (kg) | % W/W |
| 1 | Micronized trans-R,R lutein and trans-R,R zeaxanthin | | 6.28 | 35 |
| 2 | Olive Oil USP | | 0.9 | 5 |
| 3 | MCT Oil | | 9.2 | 51 |
| 4 | Mixed Tocopherol 70%-SF | | 0.36 | 2 |
| 5 | Thyme Oil | | 0.18 | 1 |

12

-continued

| | | Batch size 18.0 kg | | |
|---|---|---|---|---|
| Sr. No | Name of the Ingredient | | Standard Quantity (kg) | % W/W |
| 6 | Linseed oil (flaxseed oil) | | 0.36 | 2 |
| 7 | D-Limonene | | 0.36 | 2 |
| 8 | Lecithin (Phosphatidylcholine) | | 0.36 | 2 |

A weighted quantity of micronized marigold paprika extract concentrate (6.28 kg) containing 80.97% xanthophyll content (by spectrophotometric & HPLC method) was used to make formulation as oil suspensions. The micronized marigold paprika extract concentrate was mixed by adding oil (9.2 kg) medium Chain triglycerides (MCT) with 14% (2.52 kg) other ingredients as olive oil, thyme oil, linseed oil (flaxseed oil), D-Limonene, Lecithin (Phosphatidylcholine) (Obtained from Sunflower), mixed tocopherol by using ball mill at room temperature. The mixture was sieved and unloaded (18 kg) analyzed for containing particle size (DV90) 2.62 μm and xanthophyll content was 28.23% by weight (UV/Vis-spectrophotometry) out of which the contents of trans-R,R lutein and trans-R,R zeaxanthin were 22.6%, and 4.71% and area % of trans-R,R lutein and trans-R,R zeaxanthin were 80.16%, and 16.68% respectively as determined by normal phase HPLC analysis.

Example 03

Beadlet preparation (15%); Batch Size 24.2 kg

| Stages | Ingredients | (% w/w) |
|---|---|---|
| Cake Phase | Micronized trans-R,R lutein and trans-R,R zeaxanthin | 24.2 |
| | Dichloromethane (MDC) | 895 |
| | Tocopherol | 2.42 |
| Water Phase | Modified starch | 53.8 |
| | Sodium Ascorbate | 2.5 |
| | Water | 274.0 |
| Powder catch | Starch N 200 | 17.5 |
| | Batch Size | 100 |
| | Set assay | 17.0 |
| | % Solid in ATFE Solution | 23.18 |
| | Total Solution quantity | 1251.0 |

Procedure:
A. A micronized marigold paprika extract concentrate was dissolved into methylene dichloride followed by addition of Tocopherol under stirring. The solution was warmed for 30 min at 40-45° C. till it becomes clear and further cooled to room temperature. The solution was filtered to get clear brownish colored solution.
B. Modified starch was dissolved in water and warmed up to 50-55° C., till it becomes clear solution under stirring. Cool the aqueous system to roomtemperature.
C. Stage A solution was mixed into stage B solution under stirring and sodium ascorbate was added to the mixture.
D. Stage C solution was homogenized at 15,000-20,000 rpm for 5 min interval.
E. Stage D solution was added into rotary evaporator and methylene dichloride was removed at 60° C. in the water bath with rotation at 4 rpm under vacuum and cooled it up to room temperature.

F. 3.5 kg Starch initially dried at 105° C. for 4 hours was added into spray pan and dry ice was added to the chamber to bring the temperature down to 2° C. Spraying of stage E solution was started onto the dry starch under fluidization.

G. Coated macular carotenoid beadlets were collected by sifting stage F material and dried the beadlets into tray oven at 35° C.-40° C. and sifted the dried beadlets through mesh 60 & 40 sieves.

Example 04

Beadlet preparation (20%); Batch Size 31.7 kg

| Stages | Ingredients | Beadlets 20% w/w |
|---|---|---|
| Cake Phase | Micronized trans-R,R lutein and trans-R,R zeaxanthin | 31.7 |
| | Dichloromethane | 1172 |
| | Tocopherol | 3.2 |
| Water Phase | Modified starch | 45.2 |
| | Sodium Ascorbate | 2.5 |
| | Water | 274 |
| Powder catch | Starch N 200 | 17.5 |
| | Batch Size | 100 |
| | Set assay | 22 |
| | % Solid in ATFE Solution | 23.18 |
| | Total Solution quantity | 1528 |

Procedure:

A. Micronized marigold paprika extract concentrate was dissolved into dichloromethane followed by addition of Tocopherol under stirring. The solution was warmed for 30 min at 40-45° C. till it becomes clear and further cooled to room temperature. The solution was filtered to get clear brownish colored solution.

B. Modified starch were dissolved in water and warmed up to 50-55° C., till it becomes clear solution under stirring. Cooled the aqueous system to room temperature.

C. Stage A solution was mixed into stage B solution under stirring and sodium ascorbate was added to the mixture.

D. Stage C solution was homogenized at 15,000-20,000 rpm for 5 minutes interval.

E. Stage D solution was added into rotary evaporator and methylene dichloride was removed at 60° C. in the water bath with rotation at 4 rpm under vacuum and cooled it up to room temperature.

F. 3.5 kg Starch initially dried at 105° C. for 4 hours was added into spray pan and dry ice was added to the chamber to bring the temperature down to 2° C. Spraying of stage E solution was started onto the dry starch under fluidization.

G. Coated macular carotenoid beadlets were collected by sifting stage F material and dried the beadlets into tray oven at 35° C.-40° C. and sifted the dried beadlets through mesh 60 & 40 sieves.

14

Example 05

Beadlet preparation (10%); Batch Size 19.5 kg

| Stages | Ingredients | % W/W |
|---|---|---|
| Water Phase | Micronized trans-R,R lutein and trans-R,R zeaxanthin | 19.5 |
| | Tocopherol | 3.5 |
| | Modified starch | 54.8 |
| | Sodium ascorbate | 2.2 |
| | Water | 132 |
| Powder catch | Starch N 200 | 20.0 |
| | Batch Size | 100.0 |
| | Set assay | 13.0 |
| | % Solid in Solution | 40.00 |
| | Total Solution quantity | 1000.0 |

Procedure:

A. Disperse the Modified starch& Sodium ascorbate binder into warm water (50-55° C.) under stirring to from the clear solution.

B. Added Marigold Paprika extract Conc-Micronized and Tocopherol into Stage A dispersion under stirring to form the solution for 15 min.

C. StageB solution was processed under polytron high shear stirrer for uniform mixing of the cake into binder solution at 5000 to 12000 RPM for 15 min, observed the Temp of the solution and flow ability.

D. Added the Stage C solution into horizontal grinding mill inlet and processed it for repeated passes for size reduction and proper emulsification of solution using following process parameters.

E. After ATFE pass, Catch the solution on fluidized starch N 200 at desired process parameters.

F. Dry the beadlets in oven at 55° C. to achieve the LOD below 5%.

The Bioavailability study design for the xanthophyll composition comprising trans-R,R lutein and trans-R,R zeaxanthin in form of oil suspension was carried out as Study 1 below:

Study 1:

For ease of understanding, sample nomenclature for Product A is Micro OS R+ and Product B is Reference sample. In addition, in examples wherever lutein and zeaxanthin are mentioned, it should be considered as trans-R,R lutein and trans-R,R zeaxanthin.

Objective:

To compare the bioavailability of trans-R,R lutein 10 mg and trans-R,R zeaxanthin 2 mg from a single oral dose (oil suspension) as a Product A (Micro OS R+) with product B (Reference) formulation (trans-R,R lutein 10 mg and trans-R,R zeaxanthin 2 mg per capsule) supplementation in healthy, adult human subjects under fed conditions. Product B is a marketed product Florglo® (trans-R,R lutein) and Optisharp™ (trans-R,R zeaxanthin).

Study Design: Double blind, balanced, randomized, two-treatment, single-period, single-dose, parallel study Preparation:

Micro OS R+ sample: prepared as per example 01 in 5:1 ratio

Product B: a marketed product Florglo and Optisharp (FloraGLO® Lutein 20% SAF and OPTISHARP™ Natural (Zeaxanthin) 14% Safflower Oil were calculated and mixed to maintain the 5:1 ratio wherein trans-R,R lutein 10 mg and trans-R,R zeaxanthin 2 mg per capsule).

Number of volunteers: 90 healthy volunteers (45 volunteers per group)

Figure 1:
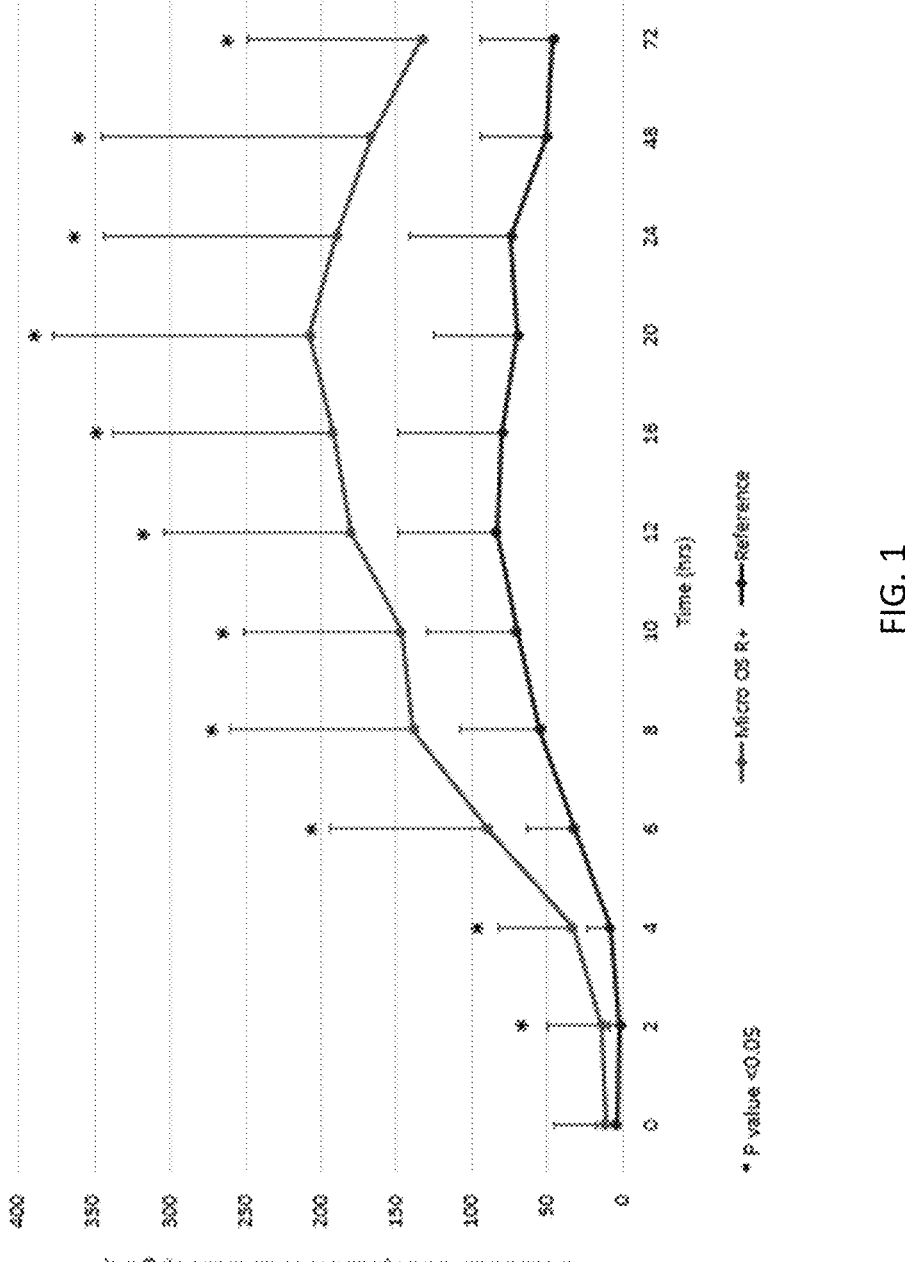
FIG. 1 shows Comparative Linear Plot of Baseline Corrected Mean±SD of Serum trans-RR lutein Concentrations vs Time for Micro OS R+ and Reference.

Housing of volunteers: 7 days housing pre and post study to control for diet with minimal amount of lutein and zeaxanthin Pharmacokinetic (PK) Assessments:

Baseline corrected Serum concentration of trans-R,R lutein and trans-R,R zeaxanthin were measured at different time points:

Time points (hours): −48, −24, 0, 2, 4, 6, 8, 10, 12, 16, 20, 24, 48 and 72 hours (P<0.05) compared to Reference group at all-time points (2 to 72 hrs) post dose. (FIG. 1)

Baseline corrected serum trans-R,R lutein concentrations for Micro OS R+ group showed more than 2× folds higher absorption at all time points and 3× folds higher absorption at Tmax (20 hrs) compared to Reference group.

Baseline Corrected Pharmacokinetic Parameters for Trans-R,R Lutein

| Parameters | Geometric Least Square Mean | | A/B Ratio (%) | 90% Confidence Interval (%) | | P-Value Transformed Log |
|---|---|---|---|---|---|---|
| | Product A Micro OS R+ (N = 45) | Product B Reference (N = 45) | | | | |
| Ln(Cmax) (ng/ml) | 219.1539 | 87.0140 | 251.86 | 191.97 | 330.44 | <.0001* |
| Ln(AUC0-72) (hr * ng/ml) | 8499.8925 | 2892.0893 | 293.90 | 217.33 | 397.46 | <.0001* |
| Ln(AUC0-T) (hr * ng/ml) | 8264.0226 | 2622.9697 | 315.06 | 224.50 | 442.17 | <.0001* |
| Tmax (hours)$ | 20.00 (4.00-72.00) | 16.00 (6.00-48.00) | — | — | — | 0.0564 |

$Median (Minimum-Maximum)
*P value <0.05

Pharmacokinetic parameters (Ln(Cmax), Ln(AUC0-72), Ln(AUC0-T and Tmax))
90% CI, T/R ratio Bioanalytical Procedure:

Lutein and Zeaxanthin (lutein comprising trans-R,R lutein and zeaxanthin comprising trans-R,R zeaxanthin) was estimated in serum using a validated HPLC method.

Results for Trans-R,R Lutein and Trans-R,R Zeaxanthin

Baseline Corrected Serum Trans-R,R Lutein Concentrations for Product a (Micro OS R+) and Product B (Reference)

| Time Points (hrs.) | Product A Micro OS R+ (N = 45) | | Product B Reference (N = 45) | | |
|---|---|---|---|---|---|
| | Arithmetic Mean | SD | Arithmetic Mean | SD | P-Value |
| 0.00 | 11.8829 | 33.66531 | 4.9148 | 13.77006 | 0.2021 |
| 2.00 | 14.4350 | 36.03639 | 2.4143 | 6.83637 | 0.0305* |
| 4.00 | 33.7202 | 48.52837 | 9.0962 | 15.06611 | 0.0016* |
| 6.00 | 89.4877 | 103.83044 | 32.2815 | 31.06571 | 0.0006* |
| 8.00 | 138.4649 | 121.92331 | 55.1417 | 52.78092 | <.0001* |
| 10.00 | 147.0603 | 103.61156 | 70.7683 | 59.17610 | <.0001* |
| 12.00 | 180.3070 | 124.17764 | 83.4900 | 64.75716 | <.0001* |
| 16.00 | 192.2944 | 144.60898 | 80.1977 | 68.75500 | <.0001* |
| 20.00 | 207.8854 | 168.85120 | 70.0933 | 55.60889 | <.0001* |
| 24.00 | 190.2843 | 152.47004 | 74.3409 | 66.74332 | <.0001* |
| 48.00 | 167.3378 | 178.20127 | 50.8520 | 44.00988 | <.0001* |
| 72.00 | 132.5861 | 115.34769 | 46.2418 | 48.66596 | <.0001* |

*P value <0.05

Baseline corrected serum trans-R,R lutein concentrations for Micro OS R+ group were significantly higher Micro OS R+ group showed significantly higher absorption for trans-R,R lutein compared to Reference group as evident from the significantly higher (P<0.05) baseline corrected Log transformed Cmax, AUC0-72 and AUC0-T.

Micro OS R+ group reached highest serum trans-R,R lutein concentration (Tmax) at 20 hrs whereas Reference group achieved highest serum trans-R,R lutein concentration at 16 hrs.

90% confidence interval for Cmax and AUC parameters were significantly higher than the 80-125% bioequivalence criteria demonstrating the significantly superior bioavailability of Micro OS R+ group over Reference group.

Folds of Test Compared to Reference for Baseline Corrected Trans-R,R Lutein PK Parameters

| Parameters | Geometric Least Square Mean | | Folds of Test compared to Reference |
|---|---|---|---|
| | Product A Micro OS R+ | Product B Reference | |
| Ln(Cmax) (ng/ml) | 219.1539 | 87.0140 | 2.5X |
| Ln(AUC0-72) (hr * ng/ml) | 8499.8925 | 2892.0893 | 2.9X |
| Ln(AUC0-T) (hr * ng/ml) | 8264.0226 | 2622.9697 | 3.2X |

Micro OS R+ group showed significantly higher absorption for trans-R,R lutein compared to Reference group as evident from the 2.5× folds Cmax, 2.9× folds AUC0-72 and 3.2× folds AUC0-T levels (FIG. 2 and FIG. 3).

Results for Trans-R,R Zeaxanthin

Baseline Corrected Serum trans-R,R Zeaxanthin
Concentrations for Product A (Micro OS R+) and
Product B (Reference)

| Time | Product A Micro OS R+ (N = 45) | | Product B Reference (N = 45) | | |
|---|---|---|---|---|---|
| Points (hrs) | Arithmetic Mean | SD | Arithmetic Mean | SD | ANOVA P-Value |
| 0.00 | 9.4402 | 12.51823 | 6.2203 | 7.61907 | 0.1441 |
| 2.00 | 12.9155 | 19.38294 | 6.4335 | 11.56039 | 0.0572 |
| 4.00 | 20.5625 | 24.90861 | 10.8184 | 13.56510 | 0.0235* |
| 6.00 | 32.1562 | 34.49185 | 15.4633 | 15.08300 | 0.0038* |
| 8.00 | 34.0454 | 26.58597 | 18.6964 | 21.76251 | 0.0035* |
| 10.00 | 31.2432 | 18.45573 | 16.8040 | 20.00775 | 0.0006* |
| 12.00 | 33.2990 | 20.60122 | 22.8680 | 23.66415 | 0.0283* |
| 16.00 | 30.6575 | 25.63941 | 15.1527 | 21.75149 | 0.0027* |
| 20.00 | 32.3948 | 27.30477 | 11.3353 | 13.93915 | <.0001* |
| 24.00 | 29.8132 | 23.06656 | 16.8866 | 20.41164 | 0.0060* |
| 48.00 | 38.9101 | 38.84572 | 18.0805 | 20.09565 | 0.0019* |
| 72.00 | 38.3075 | 31.39057 | 23.5634 | 25.88299 | 0.0171* |

*P value <0.05

Baseline corrected serum trans-R,R zeaxanthin concentrations for Micro OS R+ group were significantly higher (P<0.05) compared to Reference group between 4 to72 hrs time points post dose. (FIG. 4).

Baseline corrected serum trans-R,R zeaxanthin concentrations for Micro OS R+ group showed more than 1.5× folds higher absorption at all time points and 2.9× folds higher absorption at Tmax (20 hrs) compared to Reference group.

Baseline Corrected Pharmacokinetic Parameters for Trans-R,R Zeaxanthin

| Parameters | Geometric Least Square Mean | | A/B Ratio (%) | 90% Confidence Interval (%) | | P-Value Transformed Log |
|---|---|---|---|---|---|---|
| | Product A Micro OS R+ (N = 45) | Product B Reference (N = 45) | | | | |
| Ln(Cmax) (ng/ml) | 56.9452 | 32.5522 | 174.93 | 140.70 | 217.50 | <.0001* |
| Ln(AUC0-72) (hr * ng/ml) | 1929.9318 | 861.6456 | 223.98 | 159.64 | 314.26 | 0.0002* |
| Ln(AUC0-T) (hr * ng/ml) | 1817.2934 | 814.1689 | 223.21 | 154.35 | 322.79 | 0.0005* |
| Tmax (hours)$ | 20.00 (0.00-72.00) | 24.00 (0.00-72.00) | — | — | — | 0.7866 |

$Median (Minimum-Maximum)
*P value <0.05

Micro OS R+ group showed significantly higher absorption for trans-R,R zeaxanthin compared to Reference group as evident from the significantly higher (P<0.05) baseline corrected Log transformed Cmax, AUC0-72 and AUC0-T.

Micro OS R+ group reached highest serum trans-R,R zeaxanthin concentration (Tmax) at 20 hrs whereas Reference group achieved highest serum concentration at 24 hrs.

90% confidence interval for Cmax and all AUC parameters were significantly higher than the 80-125% bioequivalence criteria demonstrating the significantly superior bioavailability of trans-R,R zeaxanthin from Micro OS R+ group over Reference group.

Folds of Test Compared to Reference for Baseline Corrected Trans-R,R Zeaxanthin PK Parameters

| Parameters | Geometric Least Square Mean | | Folds of Test |
|---|---|---|---|
| | Product A Micro OS R+ | Product B Reference | compared to Reference |
| Ln(Cmax) (ng/ml) | 56.9452 | 32.5522 | 1.7X |
| Ln(AUC0-72) (hr * ng/ml) | 1929.9318 | 861.6456 | 2.2X |
| Ln(AUC0-T) (hr * ng/ml) | 1817.2934 | 814.1689 | 2.2X |

Micro OS R+ group showed significantly higher absorption for trans-R,R zeaxanthin compared to Reference group as evident from the 1.7× folds Cmax and 2.2× folds AUC0-72 & AUC0-T levels.

Conclusion of Study on Oil Suspension (Micro OS R+; Product A) Composition

Micro OS R+(Product A) composition showed significantly higher absorption for trans-R,R Lutein in the range of 2.9 to 3.2 folds and trans-R,R zeaxanthin in 2.2 folds when compared to Reference (Product B) composition in terms of achieving higher serum concentration at multiple timepoints measured post dose; higher absorption, 90% confidence interval for Cmax and all AUC parameters were significantly higher than the 80-125% bioequivalence criteria demonstrating the significantly superior bioavailability of Micro OS R+ group over Reference group.

Abbreviations

Terms Meaning

Cmax Highest concentration of an investigational product in the serum

AUC0-72 Area under the serum concentration versus time curve, from time 0 to 72 hours AUC0-t Area under the serum concentration versus time curve, from time 0 to last measurable concentration Tmax Amount of time that an investigational product is present at the maximum concentration in serum

We claim:

1. A xanthophyll composition comprising:
a) trans-R,R lutein in a range of about 65-85% by weight;
b) trans-R,R zeaxanthin in a range of about 10-30% by weight;
c) one or more carriers or vehicles in a range of about 20-80% by weight, wherein the one or more carriers or vehicles is selected from medium chain triglycerides (MCT) oil, sunflower oil, coconut oil, corn oil, cottonseed oil, canola oil, palm oil, peanut oil, safflower oil, sesame oil, soybean oil, rapeseed oil, and a mixture thereof;
d) one or more solubility enhancers in a range of about 1-10% by weight;
e) optionally one or more flavoring agents in a range of about 1-5% by weight;
f) one or more bioavailability enhancing agents in a range of about 1-10% by weight, wherein the one or more bioavailability enhancing agents is selected from phosphatidyl choline, nigella, caraway oil, and a mixture thereof; and
g) one or more antioxidant agents in a range of about 1-10% by weight;
wherein the trans-R,R lutein and trans-R,R zeaxanthin are obtained by a two-step extraction and purification process comprising: (i) extracting marigold flowers and paprika fruit pods with a food-grade solvent to obtain marigold and paprika oleoresins rich in lutein esters and R,R-zeaxanthin esters, respectively; and (ii) treating the oleoresins with an aqueous alcoholic alkali solution to effect saponification, thereby converting lutein esters and R,R-zeaxanthin esters to free trans-R,R lutein and trans-R,R zeaxanthin, followed by extraction, purification, and isolation to obtain a marigold and paprika extract concentrate comprising at least 80% by weight of trans-R,R lutein and at least 15% by weight of trans-R,R zeaxanthin, and are present in a ratio of 4:1 to 6:1,
wherein the isolated and purified xanthophylls are micronized using a jet mill to obtain a particle size of the trans-R,R lutein and trans-R,R zeaxanthin in a range of 0.1-10 microns, and
wherein said composition is free from R,S zeaxanthin and S,S zeaxanthin.

2. The xanthophyll composition according to claim 1, wherein the one or more solubility enhancers is selected from the group consisting of thyme oil, olive oil, linseed oil, and a mixture thereof.

3. The xanthophyll composition according to claim 1, wherein the one or more antioxidants is selected from the group consisting of tocopherol, sodium ascorbate, and a mixture thereof.

4. The xanthophyll composition according to claim 1, wherein the composition comprises a particle size ranging from about 0.1-10 micron.

5. The xanthophyll composition according to claim 1, wherein the xanthophyll composition has increased bioavailability of 1.5-4 folds against a reference composition, wherein the reference composition is obtained from marigold.

6. The xanthophyll composition according to claim 1, wherein the xanthophyll composition has increased concentrations in serum in 2-4 times against a reference composition, wherein the reference composition is obtained from marigold.

7. The xanthophyll composition according to claim 1, wherein the xanthophyll composition is in a form selected from the group consisting of beadlets, powders, oil suspension, granules, capsules, tablets, and films.

8. The xanthophyll composition according to claim 1, wherein the xanthophyll composition is in an oil suspension.

9. The xanthophyll composition according to claim 7, wherein the oil suspension is prepared by a method comprising the following steps:
a) obtaining trans-R,R lutein and trans-R,R zeaxanthin from marigold and paprika oleoresins, respectively, with a selective ratio of 4:1 to 6:1;
b) micronizing trans-R,R lutein and trans-R,R zeaxanthin from step (a) using air jet mill to obtain a particle size in a range of about 0.1-10 micron;
c) mixing micronized trans-R,R lutein and trans-R,R zeaxanthin obtained in step (b) with a carrier or vehicle;
d) adding a solubility enhancer to step (c) along with a flavoring agent;
e) adding a bioavailability enhancing agent and an antioxidant agent to step (d) to obtain a suspension;
f) mixing the suspension obtained in step (e) using ball mill to obtain a homogenous oil suspension; and
g) sieving the homogenous oil suspension obtained in step (f) to obtain a desired particle size of the oil suspension.

10. The xanthophyll composition according to claim 8, wherein the beadlets are prepared by a method comprising the following steps:
a) obtaining trans-R,R lutein and trans-R,R zeaxanthin from marigold and paprika oleoresins, respectively, with a selective ratio of 4:1 to 6:1;
b) micronizing trans-R,R lutein and trans-R,R zeaxanthin from step (a) using air jet mill to obtain a particle size in a range of about 0.1-10 micron;
c) dissolving micronized trans-R,R lutein and trans-R,R zeaxanthin in methylene dichloride followed by adding an antioxidant, and optionally a bioavailability enhancing agent, and warming followed by cooling a solution thus obtained, followed by filtering to obtain a clear brownish colored solution;
d) dissolving modified starch in water and warming until it becomes a clear solution and cooling to room temperature;
e) mixing the solution obtained in step (c) with the solution obtained in step (d) by stirring to obtain a mixture, and adding sodium ascorbate to the mixture under homogenization;
f) adding the solution obtained in step (e) into a rotary evaporator, under vacuum, to remove methylene dichloride, followed by cooling the resultant solution;
g) spraying the solution obtained in step (f) onto dry starch under fluidization; and
h) collecting coated macular carotenoid beadlets followed by drying to obtain the beadlets.

11. The xanthophyll composition according to claim 7, wherein the beadlets are prepared by a method comprising the following steps:
a) obtaining trans-R,R lutein and trans-R,R zeaxanthin from marigold and paprika oleoresin, respectively, with a selective ratio of 4:1 to 6:1;
b) micronizing trans-R,R lutein and trans-R,R zeaxanthin from step (a) using air jet mill to obtain a particle size in a range of about 0.1-10 micron;
c) dispersing modified starch and sodium ascorbate into warm water to from a clear solution;
d) adding micronized tocopherol to the dispersion obtained in step (c); and e) processing under polytron high shear stirrer for uniform mixing and passing through horizontal grinding mill for size reduction to obtain the beadlets.

12. The xanthophyll composition according to claim 1, wherein the ratio of trans-R,R lutein and trans-R,R zeaxanthin is 5:1.

5

\* \* \* \* \*